United States Patent [19]
Fischell et al.

[11] Patent Number: 5,242,414
[45] Date of Patent: Sep. 7, 1993

[54] ERGONOMIC VASCULAR ACCESS NEEDLE

[76] Inventors: Robert E. Fischell, 14600 Viburnum Dr., Dayton, Md. 21036; David R. Fischell, 71 Riverlawn Dr., Fair Haven, N.J. 07704; Tim A. Fischell, 513 Cherry Ave., Los Altos, Calif. 94022

[21] Appl. No.: 926,277

[22] Filed: Aug. 10, 1992

[51] Int. Cl.⁵ .......................................... A61M 5/178
[52] U.S. Cl. .................... 604/168; 604/164; 604/900; 604/167; 604/272
[58] Field of Search ............... 604/165, 168, 900, 164, 604/256, 272, 158, 167

[56] References Cited

U.S. PATENT DOCUMENTS

| | | | |
|---|---|---|---|
| 2,658,511 | 11/1953 | Furnell | 604/900 |
| 3,727,613 | 4/1973 | Sorenson et al. | 604/168 |
| 3,811,441 | 5/1974 | Sarnoff | 604/900 |
| 4,274,408 | 6/1981 | Nimrod | 604/168 |
| 4,534,763 | 8/1985 | Gettig et al. | 604/900 |
| 4,832,696 | 5/1989 | Luther et al. | 604/168 |

FOREIGN PATENT DOCUMENTS 681640 3/1964 Canada ................... 604/900

*Primary Examiner*—John G. Weiss
*Attorney, Agent, or Firm*—Morton J. Rosenberg; David I. Klein

[57] ABSTRACT

An ergonomic vascular access needle (10) is provided which has a transparent body (20) having an extended and small diameter capillary lumen (22) through which blood may be observed. The extended capillary lumen (22) is in fluid communication on opposing ends with a variable volume chamber (25) and a needle lumen (32). A movable plunger (40) within the transparent body (20) is displaceable to create the variable volume chamber (25). The distal end of the needle (30) is then pushed through the patient's skin and the plunger (40) is displaced from a forward position to create a suction within the capillary lumen (22), the needle lumen (32) and the variable volume chamber (25). The needle (30) is then advanced until the needle distal opening (33) is within the venous lumen and blood is observable in the capillary lumen (22). A guide wire (50) is then advanced through a lumen (42) of the plunger (40) which causes a plug (47) to be pushed into the variable volume chamber (25) and a guide wire (50) is then advanced into the venous lumen. In this manner, the guide wire (50) may be inserted into the venous lumen without external squirting of the blood.

14 Claims, 3 Drawing Sheets

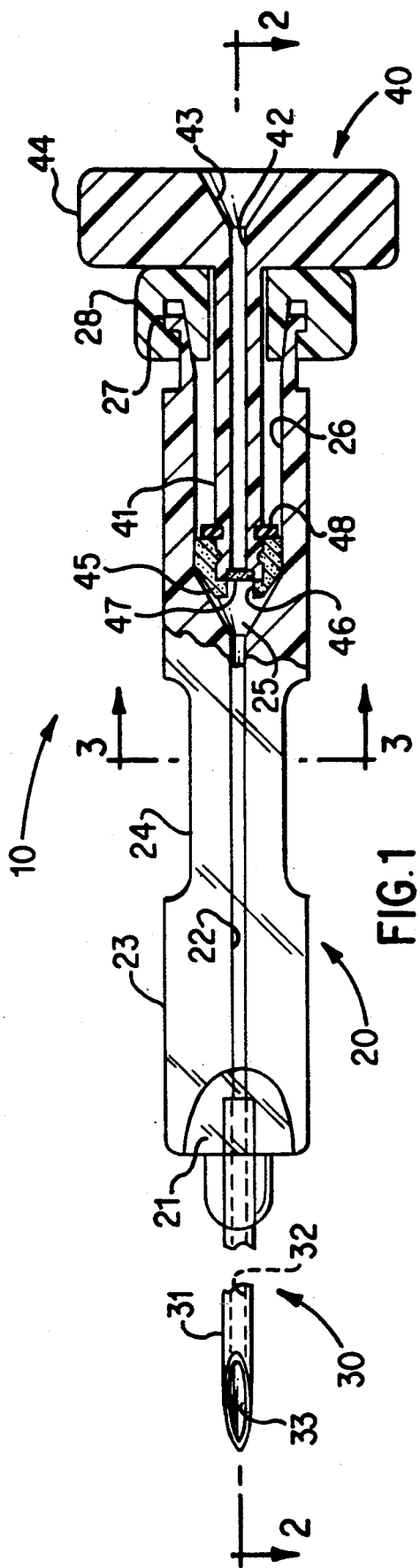
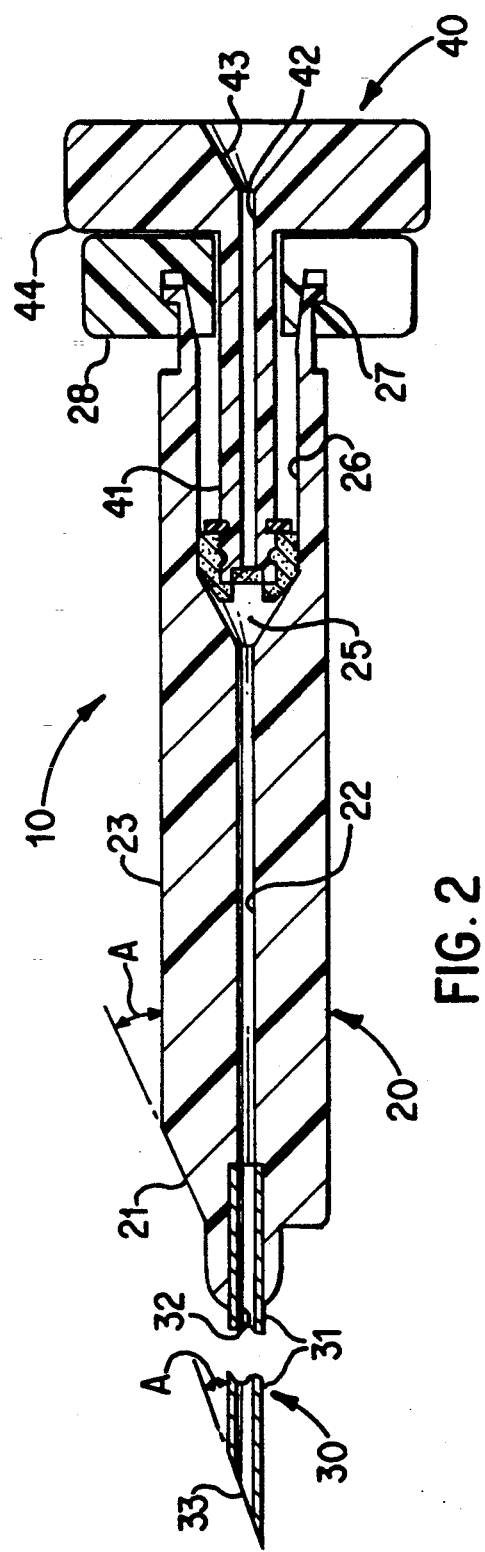
FIG. 1
FIG. 2

ERGONOMIC VASCULAR ACCESS NEEDLE

This device is in the field of means and methods for accessing human blood vessels for a multiplicity of purposes including the placement of guide wires, introducer sheaths and catheters.

BACKGROUND OF THE INVENTION

Interventional cardiologists and radiologists currently practice a wide range of procedures that require percutaneous access to the human vascular system. In many of these procedures, percutaneous access occurs at the site of the common femoral artery or vein at the groin for the purpose of passing guide wires and introducer sheaths. Catheters can then be advanced through these sheaths to many places within the human vascular system.

One method for performing this procedure utilizes a hollow steel cannula with a separate sharpened stylet needle through its center which is pushed through skin and then completely through the common femoral artery. The stylet is then removed and the steel cannula is pulled back slowly until blood under arterial pressure squirts vigorously in a pulsatile manner out of the cannula's proximal end thus indicating that the cannula's distal end is properly placed within the artery. A guide wire is then placed through the cannula and advanced into the artery, and then the cannula is pulled out. A variety of introducer sheaths and/or catheters can then be advanced over the guide wire and into the arterial system.

Another method for accessing arteries is by means of an introducer needle with a sharpened distal end that does not use a stylet needle. This introducer needle is placed through the skin at the groin and advanced until the opening of its sharpened distal end lies within the arterial lumen. When this occurs, blood squirts forcibly in a pulsatile manner out of the needle's proximal end. The pulsatile blood flow indicates that the introducer needle is properly located in the artery so that a guide wire can be inserted through the introducer needle.

One disadvantage of existing needles is that they have a short, square cross section, optically opaque, plastic handle (or body) which is not comfortable to hold when pushing the needle's sharpened distal end through skin and tissue at the groin. In fact, a typical plastic handle would be approximately 0.8 inches long and would have sharp corners molded into the plastic which are not comfortable to hold while applying considerable squeezing force between the thumb and forefinger while inserting the needle.

Furthermore, because of their short length and opaque body, one cannot see the blood before it squirts out of the needle (when the tip is placed in an artery) until the blood is actually squirting out. The blood squirting out of the cannula at arterial pressure results in a considerable release of blood which can find its way into the eyes, nose, or other mucosal membranes of health care workers in close proximity to the patient. Besides being messy and causing unnecessary blood loss to the patient, the squirted out blood represents a risk to the health care workers who could be exposed to infectious diseases such as HIV carried in the patients blood. Thus minimizing the blood squirting out of the proximal end is highly desirable.

Furthermore, no existing vascular access needles have an indicator as to the angle of the plane of the opening at the needle's distal end. Still further, existing vascular access needles require a separate syringe to be joined at their proximal end in order to create a suction when accessing veins. When accessing the jugular vein in the neck it is sometimes difficult to tell if the needle has accidentally penetrated the carotid artery instead of the hemostasis valve which causes an undesirable drag force on the guide wire as it is inserted into the blood vessel.

BRIEF SUMMARY OF THE PRESENT INVENTION

The Ergonomic Vascular Access Needle (EVAN) is designed to overcome the shortcomings of existing vascular access needles. The EVAN has a transparent body with a long, small diameter capillary lumen through which blood can be readily observed and through which a guide wire can be inserted after the EVAN needle's distal opening has been placed in the lumen of a blood vessel. Unlike presently used vascular access needles which typically have a body length of less than 1 inch, the EVAN would typically have a body length which is ideally greater then 2.5 inches.

When accessing an artery such as the femoral artery, the EVAN design makes it possible to determine that the needle's distal opening has been properly placed within the arterial lumen by observation of a pulsating column of blood within the extended length central capillary lumen of the EVAN's transparent body. A prior patent application (U.S. Ser. No. 874,366) filed on Apr. 27, 1992 by the present inventors entitled "Vascular Access Device with Blood Containment Capability", which is included herein by reference, describes a similar means for determining that the needle's distal opening has been properly placed in an arterial lumen. However, the invention described in that prior patent application requires a separate syringe to be joined to the device's proximal end in order to access a vein. EVAN on the other hand, has a built in syringe plunger at the proximal end which provides several operating advantages over all prior art access needles. One advantage is that an additional device (namely a separate syringe) is not required. Another advantage when accessing arteries is that, unlike the device described in the prior U.S. patent application Ser. No. 874,366, the plunger can be adjusted after the needle's distal opening has been placed in an arterial lumen so that the length of the blood column at diastole can be positioned just proximal to the needle's proximal end. This assures a maximum total length of the pulsatile blood column that can be seen by the physician as the patient's arterial blood pressure varies between systole and diastole. Furthermore, when accessing the jugular vein in the neck, the plunger can be used to cause a blood column to move to near the center of the capillary lumen. Then, if there are several centimeters of pulsatile motion of the blood column within the capillary lumen, the physician knows that the needle's distal opening was accidentally placed in the lumen of the carotid artery as opposed to the jugular vein. This is because when the jugular vein (or any other vein) is accessed, there would be very little, if any, pulsatile motion of the blood column within the capillary lumen. However, when placed in an artery there are several centimeters of length between the position of the blood column at diastole as compared to systole.

Another advantage of the EVAN's built in plunger is that the device can be flushed out (typically with sterile saline solution) without having to use a separate syringe which must also be attached and detached.

The EVAN design as described herein provides a novel plug means within the plunger which creates a pressure seal as needed for arterial and venous access and for flushing but can be pushed out of the way when a guide wire is advanced through the plunger's central lumen. After the advancing guide wire has caused the plug to be removed, there is essentially no frictional drag force as the guide wire moves into the vascular lumen. If a hemostasis valve is used as a pressure sealing means, there is some drag on the guide wire as it is advanced into the vascular lumen. One embodiment of the EVAN utilizes a plug that, after it is opened by the guide wire passage, it can be reseated by advancing the plunger to its full forward position.

Thus an object of this invention is to place a guide wire and/or introducer sheath into a blood vessel while preventing the free release of blood.

Still another object of the invention is to observe the pulsatile motion of the blood in a small diameter lumen having an extended length so that the linear displacement between diastolic and systolic blood pressure is maximized.

Still another object of this invention is to provide an optical magnification means for the small diameter lumen so that the pulsatile motion of the blood's column can be more readily observed.

Still another object of the EVAN design is its ergonomic shape which is human engineered to optimize its feel and utility for the physician who uses it.

Still another object of this invention is to have a vascular access needle with a sufficiently long and contoured body to be comfortably held in the hand while inserting the needle through the skin and into a vascular lumen which greater length also assists in accurately aiming the needle's distal opening into the lumen of a blood vessel.

Still another object of this invention is to have an angled surface indicator on the device's body which surface is parallel to the plane of the needle's distal opening.

Still another object of this invention is to have two parallel flat surfaces within the contoured body which automatically orient the needle's distal opening when the flat surfaces are held between the thumb and forefinger.

Still another object of this invention is to have a pressure tight plug in the EVAN's plunger which can be pushed aside by means of guide wire insertion.

Still another object of this invention is to have a tethered, reseatable plug in the plunger which can be opened with the guide wire and reseated by advancing the plunger to its full forward position.

These and other objects and advantages of this invention will become apparent upon careful reading of the detailed description of this invention as presented herein.

BRIEF DESCRIPTION OF THE DRAWINGS

FIG. 1 is a longitudinal, top view, partial cross section of one embodiment of the EVAN.

FIG. 2 is a longitudinal, side view, cross section of the EVAN taken at section 2—2 of FIG. 1.

DETAILED DESCRIPTION OF THE DRAWINGS

Figure 3:
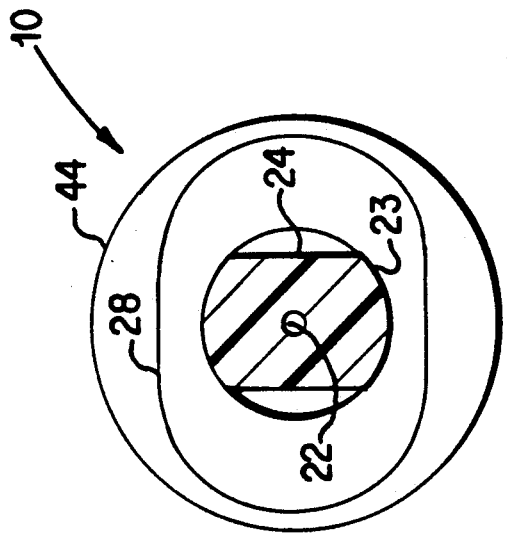
FIG. 3 is a transverse cross section of the EVAN at section 3—3 of FIG. 1.

FIGS. 1, 2, 3 and 4 illustrate one embodiment of the Ergonomic Vascular Access Needle (EVAN) 10. FIG. 1 is a top view showing a partial cross section of the EVAN 10 which consists of a transparent body 20, a hollow needle 30 and a plunger 40. The longitudinal cross-sectional view shown in FIG. 2 also shows the body 20, needle 30 and plunger 40. The body 20, has an angled surface 21 at its distal end, a central, small diameter, extended length capillary lumen 22, a cylindrical surface 23, a flat surface 24 designed to be comfortably gripped between the thumb and forefinger, a variable volume chamber 25 that lies distal to the distal end of the plunger 40, an internal cylindrical surface 26 through which the plunger's washer 45 can slide, a female Luer lock fitting 27 and a male Luer lock fitting 28. Instead of male and female Luer lock fittings, a similar construction could be permanently attached at the proximal end of the body 20. The needle 30 has a cylindrical body 31 whose proximal end is molded or adhesively joined to the distal end of the body 20 so that the needle's lumen 32 is in fluid communication with the body's lumen 22. A distal opening 33 is the distal terminus of the needle lumen 32. The plunger 40 has a cylinder 41 with a central lumen 42 which can have a tapered entry hole 43 in the plunger handle 44. At its distal end, the plunger 40 has a soft elastomer washer 45 which has a distal lumen 46 through which a plug 47 can be slid into or out of an indentation located at the distal end of the cylinder 41. A marker 48 positioned near the plunger's distal end can be used with the index marks 53 of FIG. 5 (as will be later explained) to accurately set the size of the variable volume chamber 25. The transverse cross section of the EVAN 10 shown in FIG. 3 illustrates the capillary lumen 22, the cylindrical surface 23, the flat surfaces 24, the oblong shape of the Luer lock fitting 28 and the plunger handle 44. Because of the curvature of the cylindrical surface 23 and the thickness of the transparent plastic of the body 20, the diameter of the capillary lumen 22 will be magnified so that a blood column in that lumen 22 will be more easily observed by the physician.

The needle 30 would typically be fabricated from Type 304 stainless steel with a total length of approximately 3 inches, an inside diameter of 0.040 inches and a wall thickness between 0.005 and 0.010 inches. The body 20 would typically be fabricated from a clear plastic such as polymethyl methacrylate (typically under the trade name Lucite or Plexiglas) with a length of 2 to 4 inches and a diameter between 0.2 and 0.5 inches. The capillary lumen 22 would typically have a diameter of 0.040 inches and a length of 1 to 2.5 inches. The cylindrical surface 26 would typically have an inside diameter between 0.1 and 0.4 inches and a length of 0.3 to 2.0 inches. It is important to note that the ratio of the length of the lumen 22 should be 1 to 5 times greater that the length of the cylindrical chamber formed by the cylindrical surface 26. The plunger cylinder 41 and handle 44 would typically be made from a biocompatible plastic such as polycarbonate, PVC, Nylon, Teflon or an equivalent plastic material. The plunger washer 45 and plug 47 would typically be made from an elastomer such as silicone rubber.

Although the lumen 22 is shown with a uniform inside diameter, it could be advantageously tapered with a larger diameter at its proximal end. The body 21 has parallel, flat surfaces 24 that can be gripped between the thumb and forefinger so that when the surfaces 24 are placed vertically, the opening 33 would be either up or down, but certainly not sideways. The angled surface 21 is inclined to the EVAN's longitudinal axis at an angle "A" which is the same angle that the needle opening 33 is inclined to EVAN's longitudinal axis.

Figure 4:
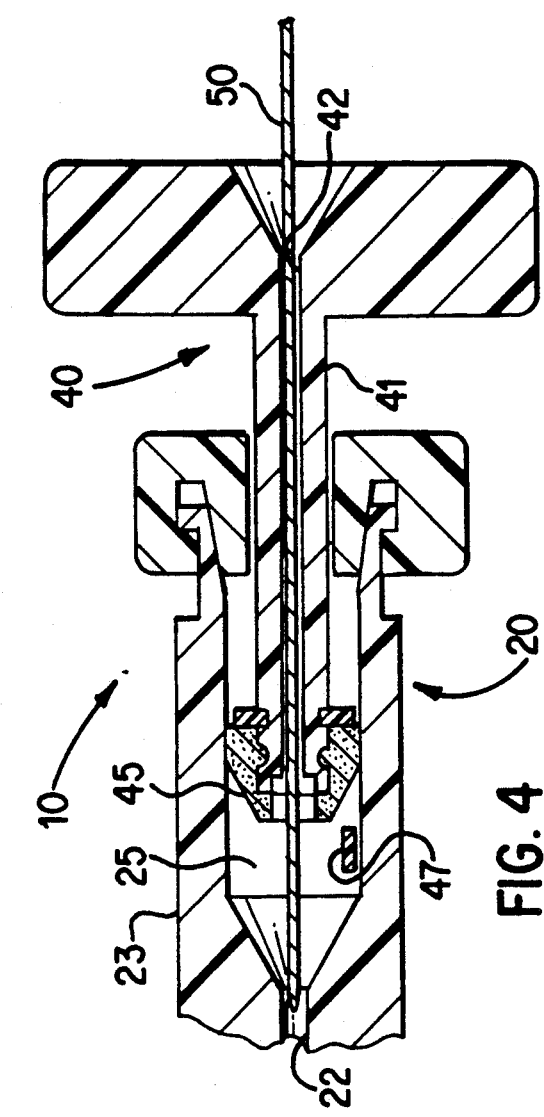
FIG. 4 is a longitudinal cross section of the EVAN's proximal end showing an inserted guide wire which has pushed the plug out if its original position.

When accessing a vein, the EVAN 10 would be used as follows:
(1) The distal end of the needle 30 is pushed through the skin and advanced a short distance.
(2) The plunger 40 is pulled back (as seen in FIG. 4) from its full forward position so as to create a suction within the lumens 22 and 32 and within the variable volume chamber 25.
(3) The needle 30 is then advanced until its distal opening 33 lies in the venous lumen which positioning is verified by the appearance of a blood column in the capillary lumen 22.
(4) A guide wire 50 (as seen in FIG. 4) is then advanced though the lumen 42 of the plunger 40 which causes the plug 47 to be pushed into the chamber 25.
(5) The guide wire is then further advanced into the venous lumen.
(6) The EVAN 10 is pulled out of the body and off the proximal end of the guide wire leaving the guide wire in place in the venous lumen.

Figure 5:
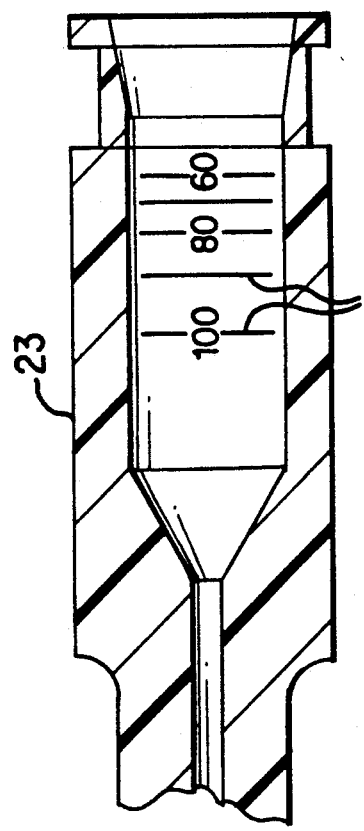
FIG. 5 shows the indicator marks for diastolic pressure on a proximal surface of the EVAN's body.

When accessing an artery, the EVAN 10 would be used as follows:
(1) The plunger 40 is pulled back until the marker 48 is positioned at an index mark 53 (as seen in FIG. 5) which approximately corresponds to the patient's diastolic pressure.
(2) The distal end of the needle 30 is then pushed through the skin and advanced until the needle's distal opening 33 lies in the arterial lumen.
(3) The physician will then observe the pulsatile motion of the blood in capillary lumen 22. If at diastole the blood column retreats into the needle lumen 32, the plunger 40 is moved slightly in the proximal direction until the blood column at diastole lies just proximal to the needle's proximal end. If the blood column extends too far in a proximal direction from the needle's proximal end, then the plunger is pushed distally until the blood column at diastole lies just proximal to the needle's proximal end.
(4) A guide wire 50 is then advanced through the EVAN 10 (as shown in FIG. 4) until it advances into the arterial lumen.
(5) The EVAN 10 is then pulled out of the body and off the guide wire 50 leaving the guide wire in place in the arterial lumen.

It should be understood that when the needle's distal opening is advanced into the artery, arterial blood pressure will cause the volume of air contained within the lumens 22 and 32 and within the chamber 25 to be compressed. The length and diameters of the lumens 22 and 32 can designed so that when the variable volume chamber is set at some specific volume, then the blood column at diastole will appear in the lumen 22 just proximal to the needle's proximal end, and at systole, the blood column can remain in the lumen 22 or might just enter the chamber 25. The position of the blood column at various pressures can be determined using the dimensions of the lumens 22 and 32 and the chamber 25, and Boyle's Law which states that $p_1 v_1 = p_2 v_2$ where:

$p_1$ = atmospheric pressure,
$p_2$ = the blood pressure,
$v_1$ = the total volume of the lumens 22 and 32 and the chamber 25, and
$v_2$ = the remaining volume at the elevated pressure of the blood.

As seen in FIG. 4, when the plug 47 is pushed out by the guide wire, blood can flow between the guide wire's outer surface and the inner surfaces of the lumens 22, 32, and 42. However, the clearance between these surfaces is typically set between 0.001 and 0.005 inches so that there is a very high resistance to blood flow. Certainly, there will be no squirting out of the blood what-so-ever before the plug is removed, and only a slight oozing of the blood after the guide wire has been placed through the lumens 22, 32 and 42.

Figure 6:
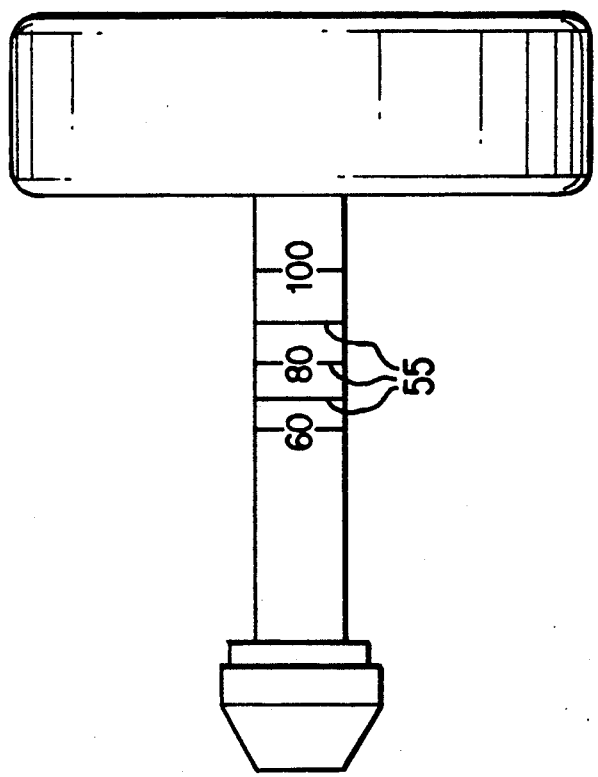
FIG. 6 shows the indicator marks for diastolic pressure on the plunger's cylindrical body.

FIG. 6 illustrates index marks on the cylinder 41 of the plunger 40 which can be used in conjunction with an indicator mark on the inside diameter of the male Luer lock fitting 28 to set the size of the variable volume chamber 25 according to the patient's diastolic pressure.

Figure 7:
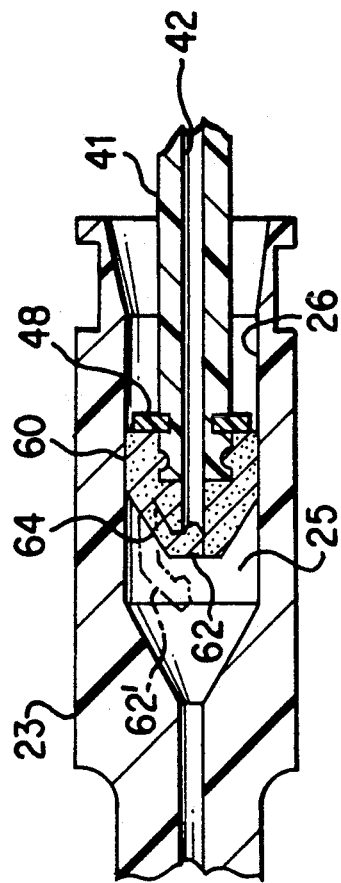
FIG. 7 illustrates the resealable plug design for the EVAN plunger.

FIG. 7 illustrates the design of a reseatable plug which is tethered to the elastomer washer placed at the plunger's distal end. FIG. 7 shows the distal portion of the plunger cylinder 41 and its lumen 42. The washer 60 is designed to provide a pressure seal against the cylindrical surface 26 of the body 20 and to move slideably within that cylindrical surface 26. A plug 62 is tethered to the washer 60 by a small elastomer tether piece 64. When the plug 62 is in place as shown by the solid lines in FIG. 7, the chamber 25 is sealed. A guide wire (not shown)can be used to push the plug 62 outward until it is in the position of plug 62' as shown by the dotted lines in FIG. 7. The guide wire can then be advanced through the lumens 22 and 32 and into the vascular lumen. After the EVAN is pulled off the guide wire, the plug 62 can be reseated to the position shown by the solid lines in FIG. 7 by pushing the plunger to its full forward position. Thus, this design for a reseatable plug would allow the EVAN to be first used to place a guide wire in a vein and then the plug could be reseated so that the EVAN could be used in an artery.

At any time when a plug seals the lumen 42 of the plunger 40, the EVAN can be flushed out (typically with sterile saline solution) by moving the plunger 40 back and forth with the needle's distal opening 33 placed in the flushing solution.

If desired, the plunger 40 can be completely removed from the body 20 by disconnecting the Luer lock fittings at the proximal end of the body 20 and pulling the plunger 40 completely out of the body 20. Thus a conventional plunger (without a plug or central lumen) could be used for vascular access and/or flushing and then the plunger could be removed for guide wire insertion. When the male Luer lock fitting is removed, a variety of medical devices could then be attached to the female Luer lock fitting 27 at the body's proximal end.

Figure 8:
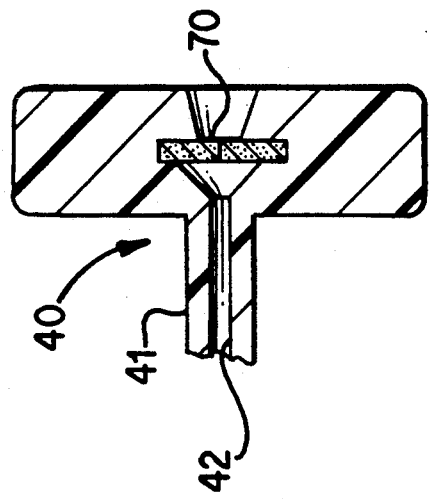
FIG. 8 illustrates a hemostasis valve design for the EVAN plunger.

FIG. 8 shows a hemostasis valve 70 mounted in the handle 44 of the plunger 40. Such a valve 70 exerts a frictional drag force on any guide wire that is placed through it. However, a hemostasis valve has a potential advantage for arterial access in that it can completely prevent even the oozing of blood out of the plunger's proximal end.

Although only chisel tipped needle designs have been discussed herein, it is envisioned that EVAN can readily utilize a sharpened, removable stylet design as is well known in the art of vascular access needles.

It should be pointed out that the EVAN 10 can be readily used for accessing the jugular vein. If when attempting to access the jugular vein, the carotid artery is inadvertently accessed, the physician will immediately know this because of the large displacement of the blood column in the capillary lumen 22 caused by the large change from diastolic to systolic blood pressure as compared to minuscule blood pressure variations that occur in a vein. The physician can then pull out of the carotid artery before any damage is done by placing a guide wire in that artery.

It should also be understood that, in order to facilitate molding of the body 20 or for any other ergonomic or aesthetic reason, the exterior surface of the body 20 may have a somewhat different shape as compared to that which is described herein.

Various other modifications, adaptations, and alternative designs are, of course possible in light of the above teachings. Therefore, it should be understood at this time that within the scope of the appended claims, the invention may be practiced otherwise than as specifically described herein

What is claimed is:

1. A vascular access device comprising:
    a thin-walled metal tube having a lumen extending freely from an opening at the tube's distal end to the tube's proximal end;
    a transparent plastic body having distal and proximal ends, the distal end forming a pressure tight seal with the metal tube's proximal end and having an extended length capillary lumen which is in fluid communication with the lumen of the metal tube, the body also having a proximal section wherein is located a cylindrical chamber, the length of the capillary lumen being greater than the length of the cylindrical chamber, and the diameter of the capillary lumen being less than one-half the diameter of the cylindrical chamber; and
    a plunger having a washer at its distal end which forms a pressure tight seal with the body's cylindrical chamber, the plunger and the washer being adapted to move slideably within the cylindrical chamber.

2. The vascular access device of claim 1 further comprising a guide wire access means within the plunger.

3. The vascular access device of claim 2 wherein the guide wire access means consists of a central lumen within the plunger and a plug which forms a pressure tight seal at the distal end of the central lumen, said plug being capable of being pushed forward into a variable volume chamber located distally to the distal end of the plunger thus forming an unobstructed central passageway through the entire length of the vascular access device.

4. The vascular access device of claim 3 wherein the plug is tethered to the plunger's distal end.

5. The vascular access device of claim 4 wherein the plug can be reseated by pushing the plunger to its full forward position.

6. The vascular access device of claim 2 wherein the central lumen of the plunger includes a hemostasis valve.

7. The vascular access device of claim 1 wherein the diameter of the capillary lumen of the body section is approximately the same diameter as the lumen of the metal tube.

8. The vascular access device of claim 1 wherein the transparent body has a thick wall and has at least one outer surface which is convex in shape; the combination of the thick wall and the convex shape resulting in optical magnification of the diameter of the capillary lumen so that the pulsating blood is more readily observable.

9. The vascular access device of claim 3 wherein the transparent plastic is polymethyl methacrylate.

10. The vascular access device of claim 1 further comprising an angled surface at the body's distal end whose plane is parallel to the plane of a chisel tip opening at the metal tube's distal end.

11. The vascular access device of claim 1 further comprising a generally cylindrical elongated body which has two flat, parallel surfaces formed near the center of the length of the body, said flat parallel surfaces being oriented so that a line normal to the plane of the opening at the metal tube's distal end is oriented parallel to the plane of said flat parallel surfaces.

12. The vascular access device of claim 1 wherein the capillary lumen of the transparent body is tapered to a larger diameter at the lumen's proximal end.

13. The vascular access device of claim 1 wherein the plunger has a marker which cooperates with index marks located on the surface of the body near its proximal end so that the plunger can be positioned to form a defined volume in the variable volume chamber which is located just distal to the plunger's distal end.

14. The vascular access device of claim 1 wherein an indicator mark located near the body's proximal end cooperates with index marks located on the surface of the plunger's cylinder so that a defined volume can be set in the variable volume chamber situated just distal to the plunger's distal

* * * * *